(12) United States Patent
Gross et al.

(10) Patent No.: US 10,059,621 B2
(45) Date of Patent: Aug. 28, 2018

(54) MAGNETIZABLE GLASS CERAMIC COMPOSITION AND METHODS THEREOF

(71) Applicant: Corning Incorporated, Corning, NY (US)

(72) Inventors: Timothy Michael Gross, Corning, NY (US); John Tyler Keech, Painted Post, NY (US); Jeffrey Glenn Lynn, Tioga, PA (US); Jinlin Peng, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 15/603,150

(22) Filed: May 23, 2017

(65) Prior Publication Data

US 2017/0341975 A1 Nov. 30, 2017

Related U.S. Application Data

(60) Provisional application No. 62/342,377, filed on May 27, 2016.

(51) Int. Cl.

| | |
|---|---|
| *C03C 10/02* | (2006.01) |
| *A61K 47/02* | (2006.01) |
| *C03C 10/00* | (2006.01) |
| *C12N 15/10* | (2006.01) |
| *C07K 1/14* | (2006.01) |
| *G01N 33/50* | (2006.01) |

(52) U.S. Cl.
CPC .......... *C03C 10/0054* (2013.01); *A61K 47/02* (2013.01); *C07K 1/14* (2013.01); *C12N 15/1006* (2013.01); *G01N 33/5091* (2013.01)

(58) Field of Classification Search
CPC . C03C 10/00; C03C 10/0036; C03C 10/0081; C04B 35/26
See application file for complete search history.

(56) References Cited

U.S. PATENT DOCUMENTS

| | | | |
|---|---|---|---|
| 4,083,727 A | 4/1978 | Andrus et al. | |
| 4,084,972 A | 4/1978 | Andrus et al. | |
| 4,126,437 A | 11/1978 | O'Horo | |
| 4,140,645 A | 2/1979 | Beall et al. | |
| 4,233,169 A | 11/1980 | Beall et al. | |
| 4,323,056 A | 4/1982 | Borrelli et al. | |
| 4,340,693 A | 7/1982 | Drake | |
| 4,889,707 A | 12/1989 | Day | |
| 5,153,070 A | 10/1992 | Andrus | |
| 5,648,124 A | 7/1997 | Sutor | |
| 5,876,452 A | 3/1999 | Athanasiou et al. | |
| 6,214,471 B1 | 4/2001 | Beall | |
| 6,506,399 B2 | 1/2003 | Donovan | |
| 6,802,894 B2 | 10/2004 | Brodkin | |
| 7,989,065 B2 | 8/2011 | Winstead | |
| 8,637,300 B2 | 1/2014 | Ruf et al. | |
| 9,056,045 B2 | 6/2015 | Hughes | |
| 9,622,483 B2 | 4/2017 | Bookbinder et al. | |
| 2004/0228905 A1 | 11/2004 | Greenspan | |
| 2008/0233201 A1 | 9/2008 | Royere | |
| 2009/0208428 A1 | 8/2009 | Hill | |
| 2012/0317735 A1 | 12/2012 | Gonzales | |
| 2012/0321567 A1 | 12/2012 | Gonzales | |
| 2013/0266625 A1 | 10/2013 | Benita | |
| 2014/0026916 A1 | 1/2014 | Havens | |
| 2014/0193499 A1 | 7/2014 | Da Fonte Ferreira | |
| 2014/0212469 A1 | 7/2014 | Rahaman | |
| 2015/0087493 A1 | 3/2015 | Ritzberger | |
| 2015/0231042 A1 | 8/2015 | Gonzales | |
| 2015/0239772 A1 | 8/2015 | Baker | |
| 2017/0086877 A1* | 3/2017 | Moffarah | A61M 25/104 |
| 2017/0340527 A1 | 11/2017 | Chang et al. | |
| 2017/0340666 A1 | 11/2017 | Deng et al. | |
| 2017/0342382 A1 | 11/2017 | Deng et al. | |

(Continued)

FOREIGN PATENT DOCUMENTS

| | | |
|---|---|---|
| CA | 2577628 C | 11/2010 |
| EP | 935526 A1 | 8/1999 |
| EP | 1021148 B1 | 5/2008 |

(Continued)

OTHER PUBLICATIONS

Raju V. Ramanujan, Book Chapter 17, Magnetic Particles for Biomedical Applications, R. Narayan (ed.), Biomedical Materials, DOI 10.1007/978-0-387-84872-3 17, C Springer Science+Business Media, LLC 2009, pp. 477-491.

International Search Report and Written Opinion PCT/US2017/034368 dated Aug. 2, 2017.

Singh et al. "Characterization of SI02-NA20-FE203-CA0-P205_B203 glass ceramics" Journal of Materials Science: Materials in Medicine, 10(8) pp. 481-484. (1999).

L. Hench et al., "Third-Generation Biomedical Materials", Science, vol. 295, Feb. 8, 2002, p. 1016-1017, www.sciencemag.org, Downloaded from www.sciencemag.org on Aug. 5, 2015.

L.L.Hench, "Bioceramics", J. Am. Ceram. Soc., 81, (7), 1705-1728 (1998).

(Continued)

*Primary Examiner* — Karl E Group

(74) *Attorney, Agent, or Firm* — Shantanu Pathak

(57) ABSTRACT

A magnetizable glass ceramic composition including:

a continuous first glass phase including $SiO_2$, $B_2O_3$, $P_2O_5$, and $R_2O$;

a discontinuous second glass phase including at least one of $SiO_2$, $B_2O_3$, $P_2O_5$, $R_2O$, or mixtures thereof; and a discrete magnetizable crystalline phase dispersed in the discontinuous second glass phase, where $R_2O$ is selected from at least one of $K_2O$, $Li_2O$, $Na_2O$, or mixtures thereof. Also disclosed are a method of making and a method of using the magnetizable glass ceramic composition.

20 Claims, 12 Drawing Sheets

(56) References Cited

U.S. PATENT DOCUMENTS

| | | | |
|---|---|---|---|
| 2017/0342383 A1 | 11/2017 | Deng et al. | |
| 2017/0349876 A1 | 12/2017 | Deng et al. | |

FOREIGN PATENT DOCUMENTS

| | | | |
|---|---|---|---|
| KR | 1007081952 | * | 8/2007 |
| WO | 2011141896 A1 | | 11/2011 |
| WO | 2012137158 | | 10/2012 |
| WO | 2014095198 A1 | | 6/2014 |
| WO | 2015034860 | | 3/2015 |
| WO | 2015123049 A1 | | 8/2015 |

OTHER PUBLICATIONS

T. Kokubo et al., "How useful is SBF in predicting in vivo bone bioactivity?", Biomaterials, 27, (2006), 2907-2915.

Qiang Fu et al., "Bioactive glass scaffolds for bone tissue engineering: state of the art and future perspectives", Materials Science and Engineering, C 31, (2011), 1245-1256.

L. Peddi et al., "Bioactive borate glass coatings for titanium alloys", J. Mater. Sci: Mater. Med., (2008), 19, p. 3145-3152.

Mohamed N. Rahaman et al., "Bioactive glass in tissue engineering", Acta Biomaterialia, 7, (2011), 2355-2373.

WO2012137158 machine translation.

Dutra Zanotto, "A bright future for glass-ceramics", American Ceramic Society Bulletin, vol. 89, No. 8, pp. 19-27.

American Type Culture Collection, Product Sheet MC3T3E1, Subclone 14, (ATCC® CRL2594™), p. 1-3, Aug. 2014.

Maziar Montazerian, et al. "History and trends of bioactive glass-ceramics", Journal of Biomedical Materials Research A, 2016, vol. 104A, 1231-1249, 2016 Wiley Periodicals, Inc.

Apel et al., "Influence of ZrO2 on the crystallization and properties of lithium disilicate glass-ceramics derived from a multi-component system", J Eur Ceram Soc, 2007, 27:1571-1577.

Antonio Tilocca et al., "Structural Effects of Phosphorus Inclusion in Bioactive Silicate Glasses", J. Phys. Chem. B 2007, 111, 14256-14264.

K. Franks et al., "The effect of MgO on the solubility behaviour and cell proliferation in a quaternary soluble phosphate baed glass system", J. of Mate. Sciemce: Materials in Medicine, 13, (2002), 549-556.

I. Ahmed et al., "Processing, characterisation and biocompatibility of iron-phosphate glass fibres for tissue engineering", Biomaterials, 25, (2004), 3223-3232.

Huipin Yuan, et al., "Osteoinduction by calciumphosphate biomaterials", Journal of Materials Science: Materials in Medicine 9 (1998) 723-726.

Jianxi Lu, et al., The Biodegradation Mechanism of Calcium Phosphate Biomaterials in Bone, Journal of Biomedical Materials Research, Aug. 2002, 63(4): 408-412.

B.C. Bunker, et al., Phosphate Glass Dissolution in Aqueous Solutions, Journal of Non-Crystalline Solids 64 (1984) 291-316.

Jonathan C. Knowles, Phosphate based glasses for biomedical applications, J. Mater. Chem., 2003, 13, 2395-2401.

Motohiro Uo et al., Properties and cytotoxicity of water soluble Na2O-CaO-P2O5 glasses, Biomaterials, 19, (1998), 2277-2284.

F. Jay Murray, Issues in Boron Risk Assessment: Pivotal Study, Uncertainty Factors, and ADIs, The Journal of Trace Elements in Experimental Medicine 9, No. 4 (1996): 231-243.

R.F. Brown, et al., "Effect of borate glass composition on its conversion to hydroxyapatite and on the proliferation of MC3T3-E1 cells." Journal of Biomedical Materials Research Part A, 88, No. 2, (2009): 392-400.

A. Saranti, et al., "Bioactive glasses in the system CaO-B2O3-P2O5: preparation, structural study and in vitro evaluation." Journal of Non-Crystalline Solids 352, No. 5 (2006): 390-398.

L. Hench, and J. Jones, eds. Biomaterials, artificial organs and tissue engineering. Elsevier, 2005—book.

E.A. Abou Neel,et al., "Effect of iron on the surface, degradation and ion release properties of phosphate-based glass fibres." Acta Biomaterialia 1, No. 5 (2005): 553-563.

E.A. Abou Neel, et al., "Characterisation of antibacterial copper releasing degradable phosphate glass fibres.", Biomaterials 26, No. 15 (2005): 2247-2254.

C. M. Rochman,et al., Scientific evidence supports a ban on microbeads, Environ Sci & Tech, 2015, 49: 10759-10761.

Wei Xiao et al., "Hollow hydroxyapatite microspheres: a novel bioactive and osteoconductive carrier for controlled release of bone morphogenetic protein-2 in bone regeneration", Acta Biomater. Sep. 2013 ; 9(9): 8374-8383.

Wanpeng Cao et al., Bioactive Materials, Ceramics International, 22, (1996) 493-507.

Fabienne C. Raszewski et al., Methods for Producing Hollow Glass Microspheres, Savannah River National Laboratory, Aiken, SC 29808, Mar. 2016.

Imogen E. Napper et al., Characterisation, quantity and sorptive properties of microplastics extracted from cosmetics, Marine Pollution Bulletin, vol. 99, Issues 1-2, Oct. 15, 2015, pp. 178-185.

Alexis J. de Kerchove et al., Formation of Polysaccharide Gel Layers in the Presence of Ca2+ and K+ Ions: Measurements and Mechanisms, Biomacromolecules, 2007, 8, 113-121.

Marianne Hiorth et al., Immersion coating of pellets with calcium pectinate and chitosan, International Journal of Pharmaceutics 308 (2006) 25-32.

Fuat Topuz, et al., Magnesium ions and alginate do form hydrogels: a rheological study, Soft Matter, 2012, 8, 4877-4881.

Yrr A. Mørch, et al., Effect of Ca2+, Ba2+, and Sr2+ on Alginate Microbeads, Biomacromolecules 2006, 7, 1471-1480.

* cited by examiner

400nm

MAGNETIZABLE GLASS CERAMIC COMPOSITION AND METHODS THEREOF

This application claims the benefit of priority under 35 U.S.C. § 119 of U.S. Provisional Application Ser. No. 62/342,377 filed on May 27, 2016 the content of which is relied upon and incorporated herein by reference in its entirety.

RELATED CO-PENDING APPLICATIONS

This application is also related commonly owned and assigned USSN Provisional Application Nos., filed concurrently herewith:

62/342,384, entitled "BIOACTIVE ALUMINOBORATE GLASSES";

62/342, 381, entitled "LITHIUM DISILICATE GLASS-CERAMIC COMPOSITIONS AND METHODS THEREOF";

62/342,391, entitled "BIODEGRADABLE MICRO-BEADS";

62/342,411, entitled "BIOACTIVE GLASS MICRO-SPHERES"; and

62/342,426, entitled "BIOACTIVE BOROPHOSPHATE GLASSES"; but does not claim priority thereto.

The present application is also related to, but does not claim priority to, commonly owned and assigned U.S. Ser. No. 61/941,677 entitled "ANTIMICROBIAL GLASS COMPOSITIONS, GLASSES AND ARTICLES INCORPORATING THE SAME", and U.S. Ser. No. 61/941,690 entitled "ANTIMICROBIAL GLASS COMPOSITIONS, GLASSES AND POLYMERIC ARTICLES INCORPORATING THE SAME," both filed Feb. 19, 2014, both mention Cu containing compositions having articles having antimicrobial properties; and U.S. Ser. No. 14/623,674, now US Pat Pub. 20150239772, entitled "LOW CRYSTALLINITY GLASS-CERAMICS", which mentions crystallizable glasses and glass-ceramics that exhibit a black color and are opaque. These materials have different alumina concentrations and different microstructures compared to the presently disclosed compositions.

The entire disclosure of each publication or patent document mentioned herein is incorporated by reference.

BACKGROUND

The disclosure relates generally to: a glass ceramic composition containing magnetite; to a magnetizable glass ceramic composition incorporating such compositions; and compositions having magnetizable attributes and articles that incorporate such glasses.

SUMMARY

In embodiments, the disclosure provides a magnetizable glass or an article made from at least a portion of the composition, which glass or article can be useful, for example, in biomedical applications.

In embodiments, the disclosed magnetizable glass composition is one of a family of glass ceramic compositions that contain ferrimagnetic magnetite crystals.

In embodiments, the disclosed magnetizable glass ceramic compositions can be ground to produce a low cost powder that can be used in a variety of biomedical applications including, for example, targeted drug delivery, magnetic hyperthermia applications, and magnetic cell separation. Small particle size distribution (PSD) magnetite particles that are currently used in these applications are very costly and can limit the scope of research in critical biomedical applications.

In embodiments, the disclosed compositions provide a cost effective alternative where, for example, large quantities of glass can be melted and ground into powder at reduced cost compared to available compositions.

In embodiments, the disclosure provides a family of glass ceramics compositions containing magnetite, which have a unique microstructure such that magnetite crystals are homogenously dispersed throughout a discontinuous phase of the glass composition.

In embodiments, the disclosed magnetic compositions and particles can have a variety of uses and applications such as mentioned herein.

BRIEF DESCRIPTION OF THE DRAWINGS

In embodiments of the disclosure.

DETAILED DESCRIPTION

Figure 1:
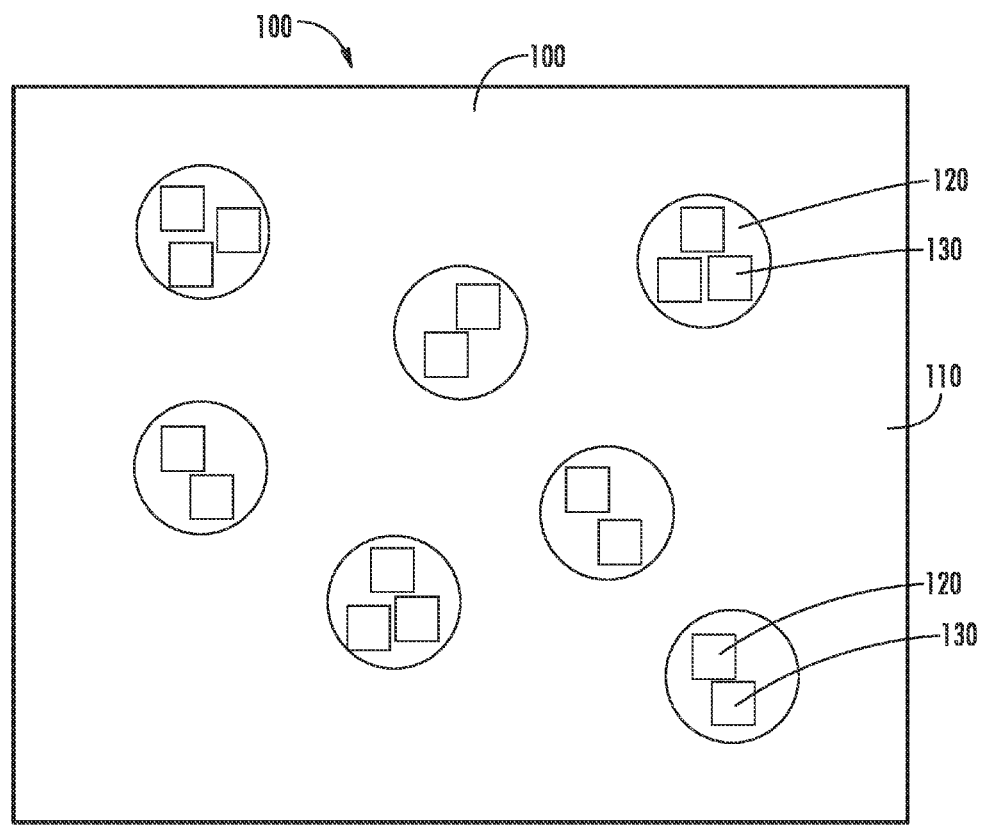
FIG. 1 shows a schematic that is representative (but not to scale or proportions) of the gross microstructure of the disclosed magnetite-containing glass ceramic (100) compositions.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

In embodiments, the disclosed compositions, articles, methods of making, and methods of using provide one or more advantageous features or aspects, including for example as discussed below. Features or aspects recited in any of the claims are generally applicable to all facets of the invention. Any recited single or multiple feature or aspect in any one claim can be combined or permuted with any other recited feature or aspect in any other claim or claims.

Definitions

"Glass," "glasses," or like terms can refer to a glass or a glass-ceramic.

"Glass article," or like terms can refer to any object made wholly or partly of a disclosed glass or a glass-ceramic.

"Particle," "microparticle," "bead," "microbead," "hollow bead," "hollow microbead," "hollow microparticle," "glass particle," "glass microparticle," or like terms refer to, for example, solid or hollow microspheres, or fragments thereof, having diameter, for example, from 1 to 1000 microns, a hollow microsphere density of from 0.1 to 1.5 $g/cm^3$, a solid microsphere density of from 0.1 to 2.5 $g/cm^3$, and a particle aspect ratio, for example, from 5:1 to 1:5.

"Magnetizable" and like terms refer to the disclosed glass-ceramic compositions or particles prepared from the compositions, which compositions become magnetic when exposed to an external magnetic field and non-magnetic in the absence of an external magnetic field. The disclosed magnetization is believed to be entirely or substantially, reversible over many magnetization cycles and over many years.

"Ferrimagnetic" and like terms refer to (in contrast to ferromagnetic materials, which are typically metals), ferrimagnetic materials, which are ceramics, in particular, ceramic oxides. The most widely used ferrimagnets in devices are materials known as ferrites. Ferrites are electrically insulating transitional-metal oxides of the general formula $MO.Fe_2O_3$, where M is a divalent ion such as $Mn^{2+}$, $Fe^{2+}$, $Co^{2+}$, or $Ni^{2+}$. Ferrites can be prepared by standard ceramic processing techniques. For example, NiO $Fe_2O_3$, powders of NiO and $Fe_2O_3$ can be mixed together and pressed into a desired shape before sintering (firing) at high temperature to form a dense ceramic of the desired composition. This method provides a reliable way of forming a wide variety of shapes and sizes of ferrimagnetic materials for incorporating into devices.

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event or circumstance can or cannot occur, and that the description includes instances where the event or circumstance occurs and instances where it does not.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "gm" for gram(s), "mL" for milliliters, and "rt" for room temperature, "nm" for nanometers, and like abbreviations).

Specific and preferred values disclosed for components, ingredients, additives, dimensions, conditions, times, and like aspects, and ranges thereof, are for illustration only; they do not exclude other defined values or other values within defined ranges. The composition and methods of the disclosure can include any value or any combination of the values, specific values, more specific values, and preferred values described herein, including explicit or implicit intermediate values and ranges.

Commonly owned and assigned U.S. Pat. No. 4,140,645, issued Feb. 20, 1979, entitled "Glasses and glass-ceramics suitable for induction heating," mentions the production of glass and glass-ceramic compositions containing a ferrimagnetic crystal phase throughout which responds thermally to fields generated by induction coils. Magnetite ($Fe_3O_4$) is the preferred ferrimagnetic crystal phase because of its high permeability and low resistivity (about $10^{-4}$ ohm-cm) at room temperature and the relative low cost of iron when compared with other ferrimagnetic species. Two general composition areas are of interest: $Na_2O$ and/or $K_2O$— $FeO$—$B_2O_3$—$SiO_2$ and $Li_2O$—$Al_2O_3$—$B_2O_3$—$SiO_2$. Where the coefficient of thermal expansion is sufficiently low to impart good thermal shock resistance, the compositions can be considered for top-of-stove cooking vessels.

Commonly owned and assigned U.S. Pat. No. 4,083,727, issued Apr. 11, 1978, entitled "Glass-ceramics with magnetic surface films," mentions the production of glass-ceramic articles, wherein the predominant crystal phase is beta-quartz solid solution and/or beta-spodumene solid solution, but which have a thin, integral, tightly-bonded surface film containing crystals exhibiting the structure of magnetite. The preferred method of production for such articles requires three general steps. First, a glass article having a particular composition within the $Li_2O$—$FeO$—$Al_2O_3$— $SiO_2$ field nucleated with $TiO_2$ is heat treated in air or other oxidizing atmosphere to yield a glass-ceramic article through the crystallization in situ of beta-quartz solid solution and/or beta-spodumene solid solution crystals. Simultaneously during this heat treatment, a surface layer containing hematite is developed. Second, the glass-ceramic article is subjected to a hot acid bath. Third, the acid-washed article is heat treated in a $H_2O$-containing reducing atmosphere to convert the hematite crystals to magnetite. The resulting films demonstrate high coercive forces and saturation magnetization comparable to that of magnetite and other ceramic ferrite materials.

U.S. Pat. No. 8,637,300, entitled "Magnetic glass particles for use in biogas plants, fermentation and separation processes," mentions a method for treating an organic and/or inorganic substrate utilizing a granular material made of a solid foam as support for an active component, for example, a biocatalyst such as a microorganism or an enzyme. The solid foam has a continuous phase in which magnetizable particles are embedded, such that the support with the biologically active component immobilized thereon can be separated from a mixture with a magnetic separation device.

In embodiments, the disclosure provides a glass ceramic composition comprising:

a continuous first glass phase comprising $SiO_2$, $B_2O_3$, $P_2O_5$, and $R_2O$;

a discontinuous second glass phase comprising at least one of $SiO_2$, $B_2O_3$, $P_2O_5$, $R_2O$, or mixtures thereof; and a discrete magnetizable crystalline phase dispersed in the discontinuous second phase, where $R_2O$ is selected from at least one of $K_2O$, $Li_2O$, $Na_2O$, or mixtures thereof.

In embodiments, the continuous first glass phase can be, for example, enriched in $SiO_2$ relative to the discontinuous second glass phase, the discrete magnetizable phase, or both.

In embodiments, the continuous first glass phase can be, for example, enriched in Si relative to the discontinuous second glass phase.

In embodiments, the discontinuous second glass phase can be, for example, enriched in Fe and P relative to the continuous first glass phase.

In embodiments, the discrete magnetic crystalline phase comprises a plurality discrete magnetite crystals comprising of at least one of $Fe^{2+}$ ions, $Fe^{3+}$ ions, $Fe^{2+}$ oxides, $Fe^{3+}$ oxides, or mixtures thereof.

In embodiments, the $R_2O$ can be, for example, $K_2O$.

In embodiments, the disclosure provides a magnetizable glass ceramic composition, comprising:

60 to 70% $SiO_2$,
1 to 2% $Al_2O_3$,
3 to 5% $P_2O_5$,
5 to 8% $B_2O_3$,
5 to 8% $R_2O$ where $R_2O$ is selected from at least one of $K_2O$, $Li_2O$, $Na_2O$, and mixtures thereof, and
10 to 22% $Fe_2O_3$, based on a composition total of 100 mol %.

In embodiments, substituting or adding $Li_2O$, $Na_2O$, or both, for $K_2O$ will promote a desired continuous and discontinuous phase separation more so than $K_2O$ alone.

In embodiments, the magnetizable glass ceramic composition can have, for example, a mol equivalent ratio of $Fe^{2+}$ to the total Fe mol equivalent ratio of from 0.4 to 0.5.

In embodiments, the magnetizable glass ceramic composition can include a plurality of iron ions in mixed oxidation states.

In embodiments, the plurality of iron ions in mixed oxidation states can comprise, for example, magnetite crystals having a size of from 0.01 to 1 micrometer.

In embodiments, the magnetizable glass ceramic composition can have magnetite crystals that are magnetized by an external magnetic field, and the resulting magnetized magnetite crystals lose magnetization in the absence of the external magnetic field.

In embodiments, the magnetizable glass ceramic composition can have a melt temperature of, for example, from 1300 to 1600° C.

In embodiments, the disclosure provides a method of making the abovementioned magnetizable glass ceramic composition, comprising:

melting a mixture of a source of:
60 to 70% $SiO_2$,
1 to 2% $Al_2O_3$,
3 to 5% $P_2O_5$,
5 to 8% $B_2O_3$,
5 to 8% $R_2O$ where $R_2O$ is selected from at least one of $K_2O$, $Li_2O$, $Na_2O$, and mixtures thereof, and
10 to 22% $Fe_2O_3$, based on a composition total of 100 mol %, and optionally reducing the size of the resulting solidified melt into a particulate powder.

In embodiments, reducing the size of the resulting solidified melt into a particulate powder can be accomplished, for example, using any suitable particle reduction or particle formation methods such as grinding, pulverizing, crushing, jet milling, melt speriodization, and like size reduction or particle formation methods.

In embodiments, the particulate powder can have, a particle size, for example, of from 1 to 100 microns, such as for example, 1 to 50, 1 to 25, 2 to 20, 3 to 10, or 3 to 5 microns, including intermediate values and ranges.

In embodiments, the particulate powder can have a particle shape selected from, for example, at least one of: a sphere having a smooth surface; a sphere having a rough surface; an irregular or random shape; a shape having an aspect ratio of 1:1 to 1:5; or a mixture thereof.

In embodiments, the melting can be accomplished, for example, at from 1300 to 1700° C., for 1 to 10 hrs.

In embodiments, the method of making can further comprise, for example, heat treating, i.e., ripening, the melt mixture at from 500 to 800° C., for 1 to 24 hrs. Ripening is optional since crystals are believed to nucleate to at least some extent during the forming and annealing steps.

In embodiments, the melt mixture can have a mol ratio, for example, of $Fe^{2+}$ to total Fe of from 0.4 to 0.5. The $Fe^{2+}$/total Fe mol ratio of 0.4 to 0.5 means 40 to 50 mol % of the Fe is 2+ and the remaining iron is $Fe^{3+}$, Fe metal, or a mixture thereof.

In embodiments, the disclosure provides an article comprising any of the above mentioned disclosed glass ceramic compositions. The article can be used in any of the above mentioned applications, for example, in biomedicine or biomedical applications.

In embodiments, the presently disclosed magnetic compositions and particles prepared from the compositions are advantaged in several aspects, including for example: an ability to be magnetized in the presence of an externally applied magnetic field; an apparently negligible residual remnant magnetization in the absence of a magnetic field; no or reduced agglomeration because of the low residual remnant magnetization; and a low cost compared to the commercially available small particle size distribution iron oxides (see for example: Agencourt AMPure XP available from Beckman Coulter®, and Dynabeads from Thermo-Fisher Scientific®).

Table 1 list examples of the disclosed glass ceramic compositions. These examples are all readily magnetized in the presence of a magnetic field. The compositions were analyzed by Inductively Coupled Plasma-Optical Emission Spectroscopy (ICP-OES). The total iron oxide content is given as mol percent $Fe_2O_3$ in Table 1. However, the total iron oxide content includes both $Fe^{2+}$ and $Fe^{3+}$ oxidation states. The redox potential was measured for the second disclosed composition and showed that the ratio of $Fe^{2+}$/total Fe mol ratio is 0.49. A mixture of $Fe^{2+}$ and $Fe^{3+}$ oxidation states is expected since both are present in magnetite crystals ($Fe^{2+}Fe^{3+}_2O_4$). The presence of magnetite ($Fe_3O_4$) (i.e., iron (II, III) oxide; ferrous-ferric oxide) was confirmed for all three glass ceramic compositions using x-ray powder diffraction (XRD).

TABLE 1

Magnetizable glass ceramic compositions analysis in wt % and mol %.

|  | first ("1") | second ("2") | third ("3") |
|---|---|---|---|
| (wt %) | | | |
| $SiO_2$ | 53.58 | 42.1 | 43.09 |
| $Al_2O_3$ | 2.55 | 2.15 | 1.64 |
| $P_2O_5$ | 7.75 | 7.25 | 5.59 |
| $B_2O_3$ | 6.8 | 6.39 | 4.67 |
| $K_2O$ | 8.72 | 8.31 | 6.31 |
| $Fe_2O_3$ | 20.6 | 33.8 | 38.7 |
| (mol %) | | | |
| $SiO_2$ | 69.09 | 60.17 | 62.41 |
| $Al_2O_3$ | 1.94 | 1.81 | 1.40 |
| $P_2O_5$ | 4.23 | 4.39 | 3.43 |
| $B_2O_3$ | 7.57 | 7.88 | 5.84 |
| $K_2O$ | 7.17 | 7.58 | 5.83 |
| $Fe_2O_3$ or total Fe | 10.00 | 18.18 | 21.09 |
| $Fe^{2+}$/total Fe ratio[1] | 0.45 | 0.49 | 0.47 |
| mol % Fe as magnetite ($Fe^{2+}Fe_2^{3+}O_4$) | 82 | 76 | 80 |

1. The maximum mol % magnetite occurs if the $Fe^{2+}$/total Fe mol ratio is 0.33. As the $Fe^{2+}$/total Fe mol ratio increases, the mol % magnetite decreases. The mol % magnetite can be calculated according to equation
(1): mol % magnetite = (1 − ($Fe^{2+}$/total Fe ratio))/0.67 (1).

FIG. 1 shows a schematic representative (but not to scale or proportions) of the microstructure of the disclosed magnetite-containing glass ceramic (100) compositions. The background or surround region (110) is the continuous matrix phase that is compositionally enriched in $SiO_2$ relative to discontinuous second glassy phases (circles) (120) and the discrete magnetite crystalline phases (squares) (130) within or encapsulated by the second glassy phases (120). The plurality of discontinuous second glass phases (120) can be enriched in $P_2O_5$ relative to the continuous matrix phase, and the boundary of the continuous matrix phase and discontinuous second glassy phases can be enriched in $R_2O$ (e.g., $K_2O$).

Figure 2:
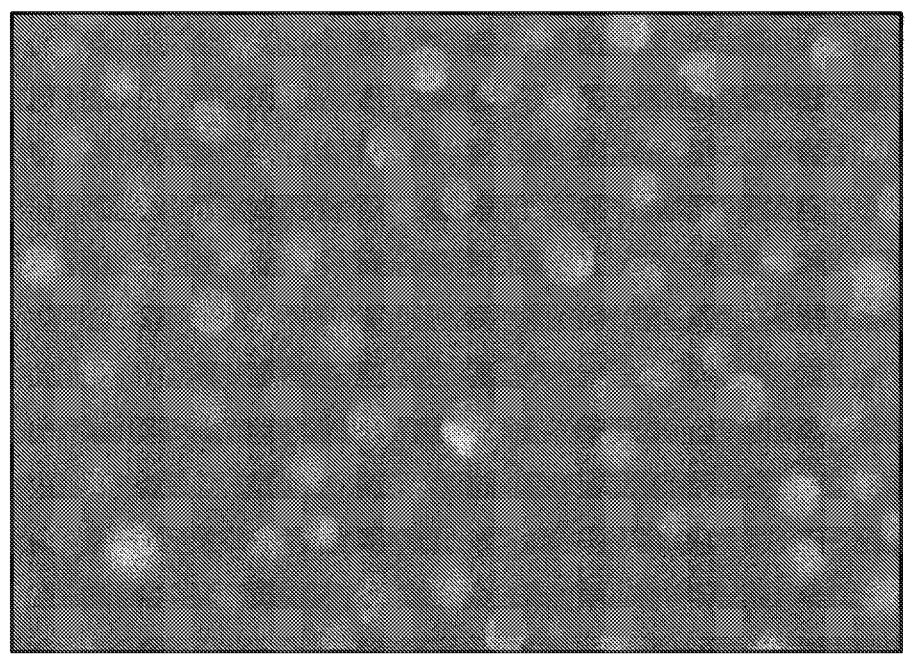
FIG. 2 shows an SEM/EDS analysis of one of the disclosed compositions ("first composition" or "1").

The first disclosed composition ("1") in Table 1 contains the least iron oxide of the three glass ceramic compositions (1, 2, and 3) that were prepared. FIG. 2 shows an SEM image with EDS analysis (not shown). The EDS analysis was done at 10 kV to decrease the electron interaction volume, and to increase the detection of iron, potassium, and phosphorus, in both the crystalline and the bright spherical phase, relative to the matrix.

Figure 3:
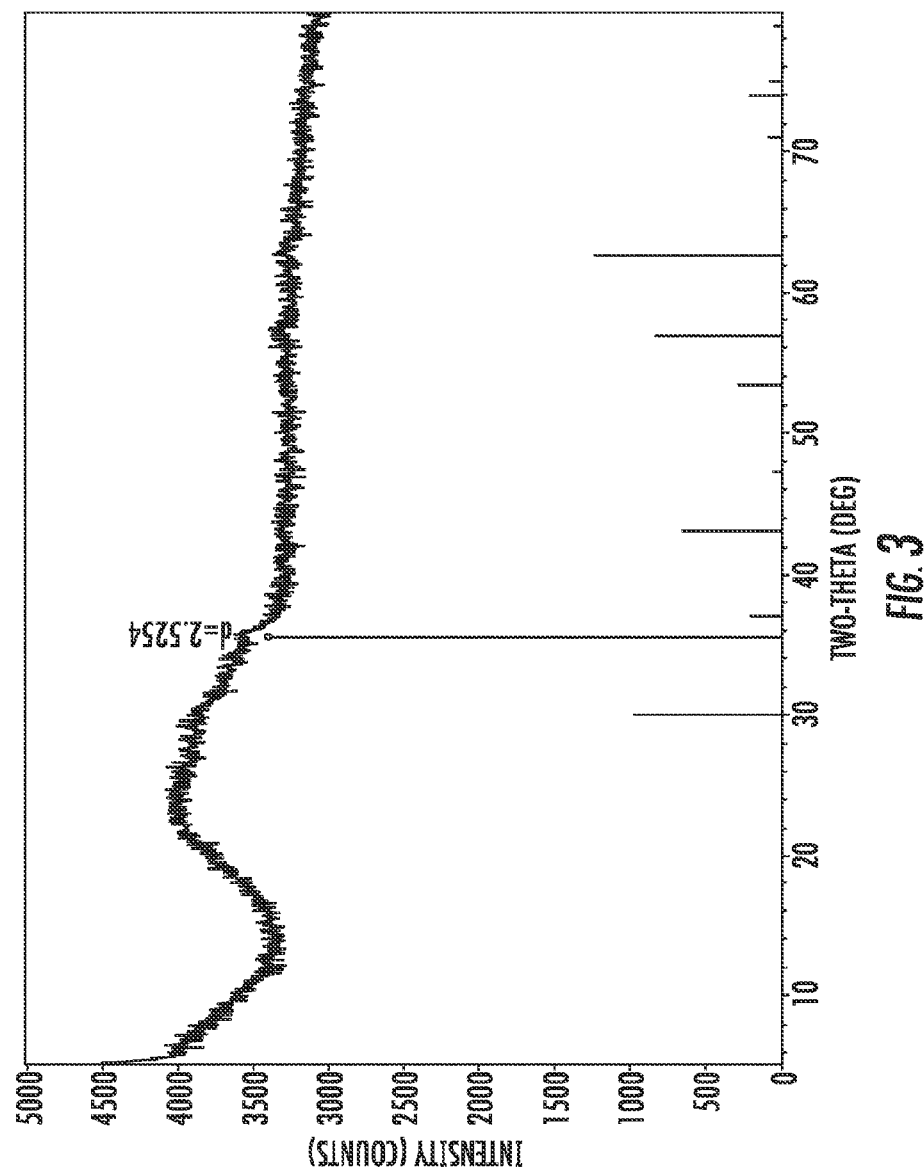
FIG. 3 shows an X-ray powder diffraction pattern of the disclosed first composition, which indicates the presence of magnetite crystals.
Figure 4:
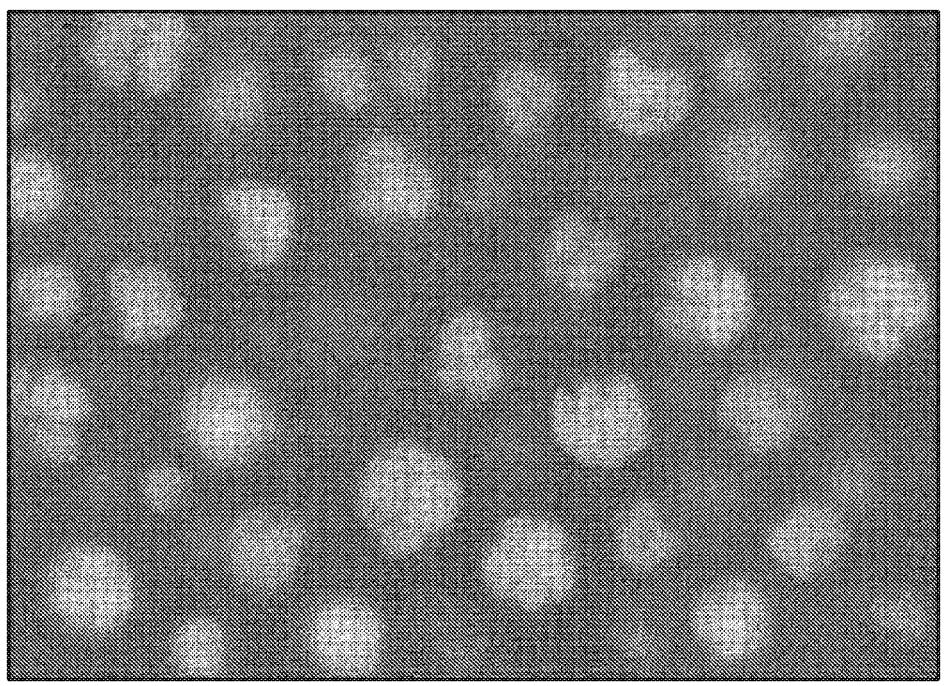
FIG. 4 shows an SEM/EDS of a second disclosed composition ("second composition" or "2"), which also indicates the presence of magnetite crystals.
Figure 12:
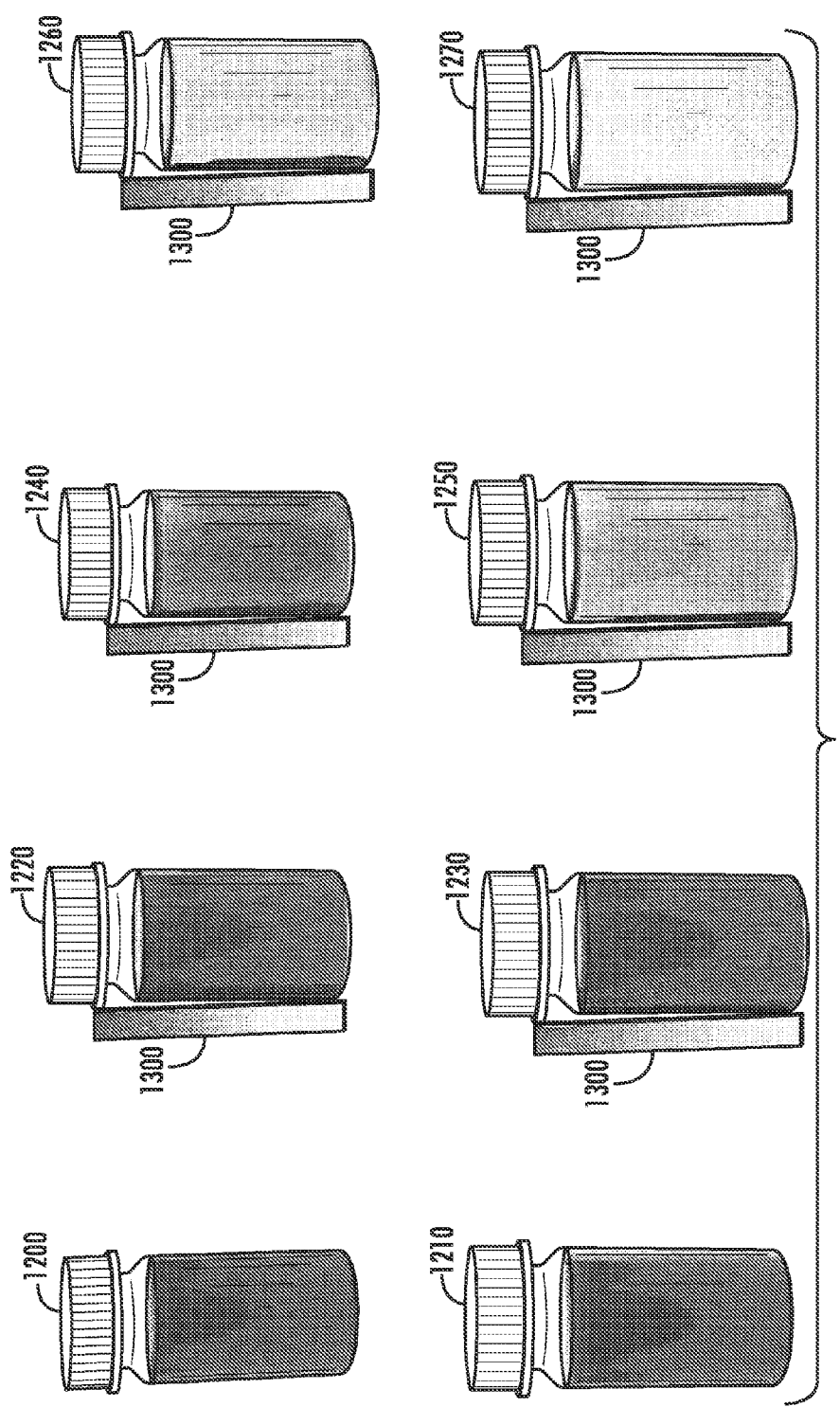
FIG. 12 show images of two different magnetizable glass ceramic compositions (top row composition "2"; and bottom row composition "3") in a magnetic separation experiment.

The structure appears to consist of three phases: 1) a glassy, continuous matrix phase; 2) a glassy, spherical, discontinuous phase; and 3) a crystalline phase that precipitates within the glassy, discontinuous phase. The EDS analysis indicates that Fe, K, and P, are enriched in the discontinuous spherical phase containing both glassy and crystalline material. The x-ray powder diffraction pattern shown in FIG. 3 indicates that magnetite is present, but the magnetic signal is relatively weak compared to the disclosed second and third compositions. Accordingly, the first disclosed composition has the lowest magnetic strength of the three disclosed glass ceramic compositions. The observed qualitative magnetic signal strengths were: "1" (composition 1)<<"2" (composition 2)≤"3" (composition 3), respectively (see FIG. 12 showing magnetic separation of suspensions of each of suspended compositions "2" and "3"). The SEM EDS analysis of the disclosed second glass ceramic composition having the intermediate level of iron oxide, is shown in FIG. 4. When compared to the SEM image of the first disclosed composition, the disclosed second composition has a better developed crystal structure.

Figure 5:
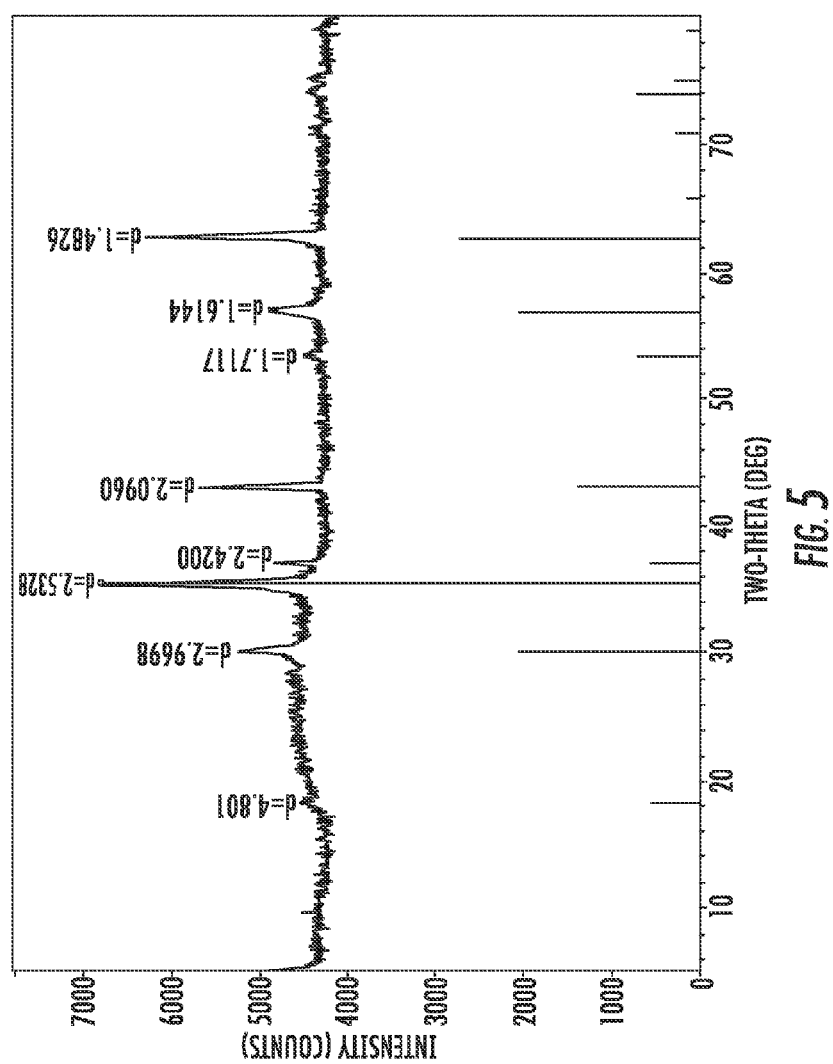
FIG. 5 shows an x-ray powder diffraction of the second disclosed composition, which indicates well defined peaks corresponding to magnetite crystals.

The structure of the disclosed second composition appears to consist of three phases: a first glassy, continuous matrix phase; a second glassy, spherical, discontinuous phase; and a crystalline phase that precipitates within the second glassy, discontinuous phase. The EDS analysis indicates enrichment of Fe and P within the spherical, discontinuous phase. FIG. 5 shows well defined peaks corresponding to magnetite crystals.

Figure 6:
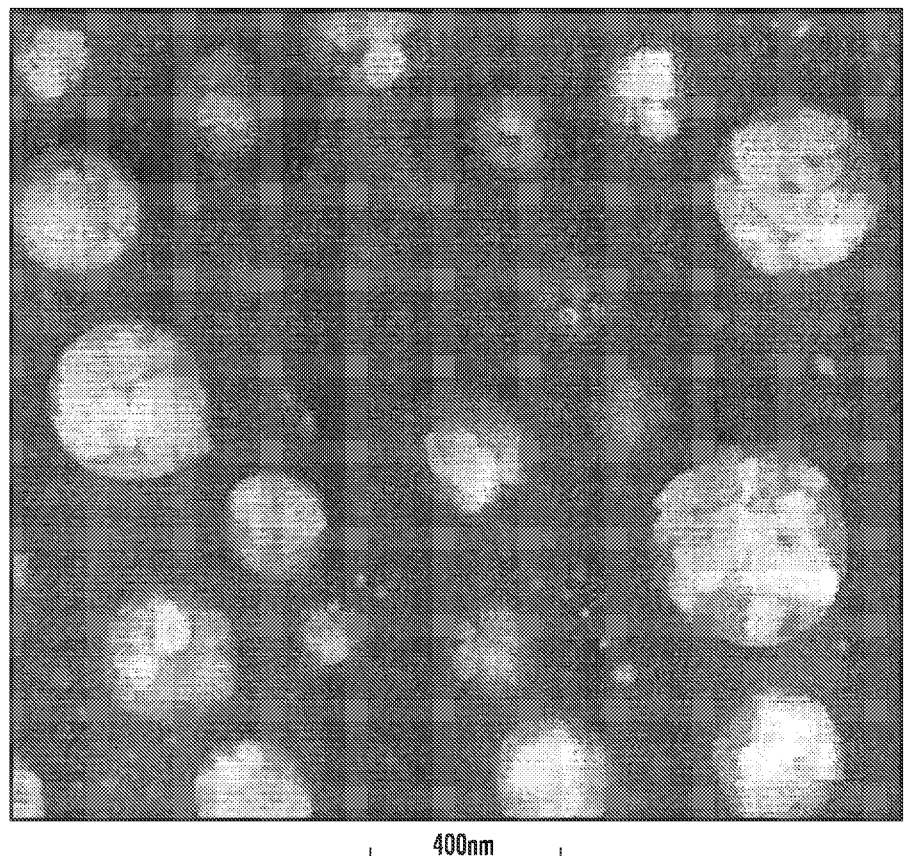
FIG. 6 shows TEM/EDS composition hyper-maps of the second disclosed composition.

As shown in FIG. 6, a TEM/EDS mapping was performed to improve the spatial resolution of the distribution of glass components when compared to an SEM/EDS. The brightest regions showing crystallinity are composed of Fe, and are identified as the magnetite crystals. The glassy phase surrounding the crystals was enriched in phosphorus. The continuous matrix phase is enriched in Si. The hypermap of the composition shows that the dispersed crystals consist of Fe and the glassy region of the discontinuous, spherical phase consists primarily of P with some enrichment of K at the periphery. There is also likely enrichment of B in the glassy region of the discontinuous, spherical phase, however, measurement limitations of the light elements preclude a definitive conclusion. The second disclosed composition was also heat treated at 750° C. for 4 hr to examine the effect of heat treatment on the microstructure. The softening point of the second disclosed composition was determined to be 831° C. using a parallel plate viscosity measurement. The heat treatment temperature of 750° C. was selected to promote crystal growth without causing sufficient deformation to the specimen.

Figure 7A:
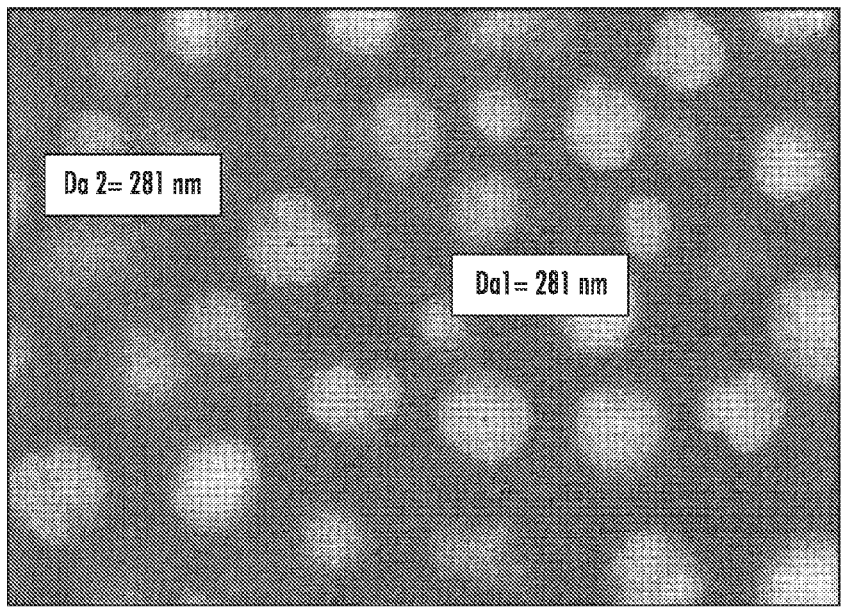
FIG. 7 shows an TEM/EDS of the second disclosed composition "as-made" (7A; top) vs. "heat treated" at 750° C. for 4 hrs (7B; bottom) demonstrating apparent thermal ripening.
Figure 7B:
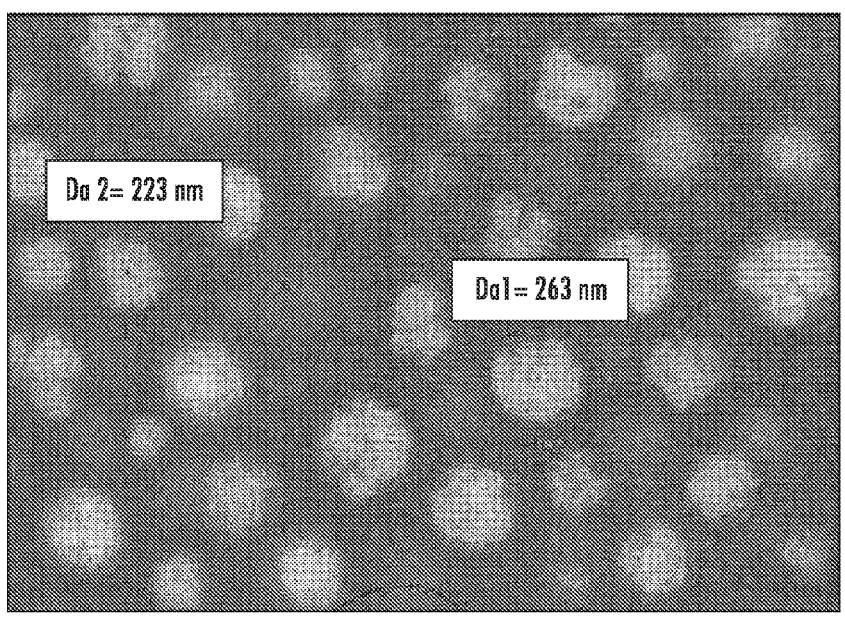

As shown in FIG. 7, the heat treatment results in phase ripening where the smallest regions of the discontinuous phase are consumed by the larger regions of the discontinuous phase. The tiny bright spots are no longer present after heat treatment and the size of the discontinuous, spherical phase regions increase on average. The heat treatment leads to a ripening effect where the smaller sized second phase regions are consumed by the larger second phase regions as the overall average size of the second phase regions grow. This reduction in overall surface area is energetically favorable.

Figure 8:
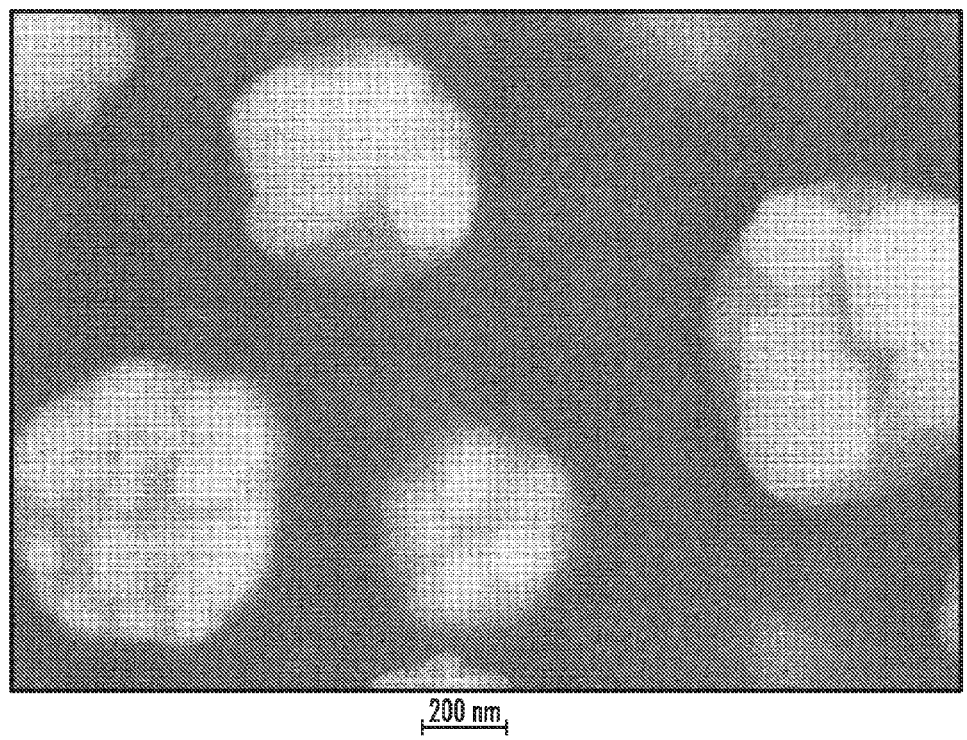
FIG. 8 shows an SEM/EDS of a third disclosed composition ("third composition" or "3"), which shows a similar microstructure to the second disclosed composition with the exception that the spherical discontinuous phase has a larger diameter.
Figure 9:
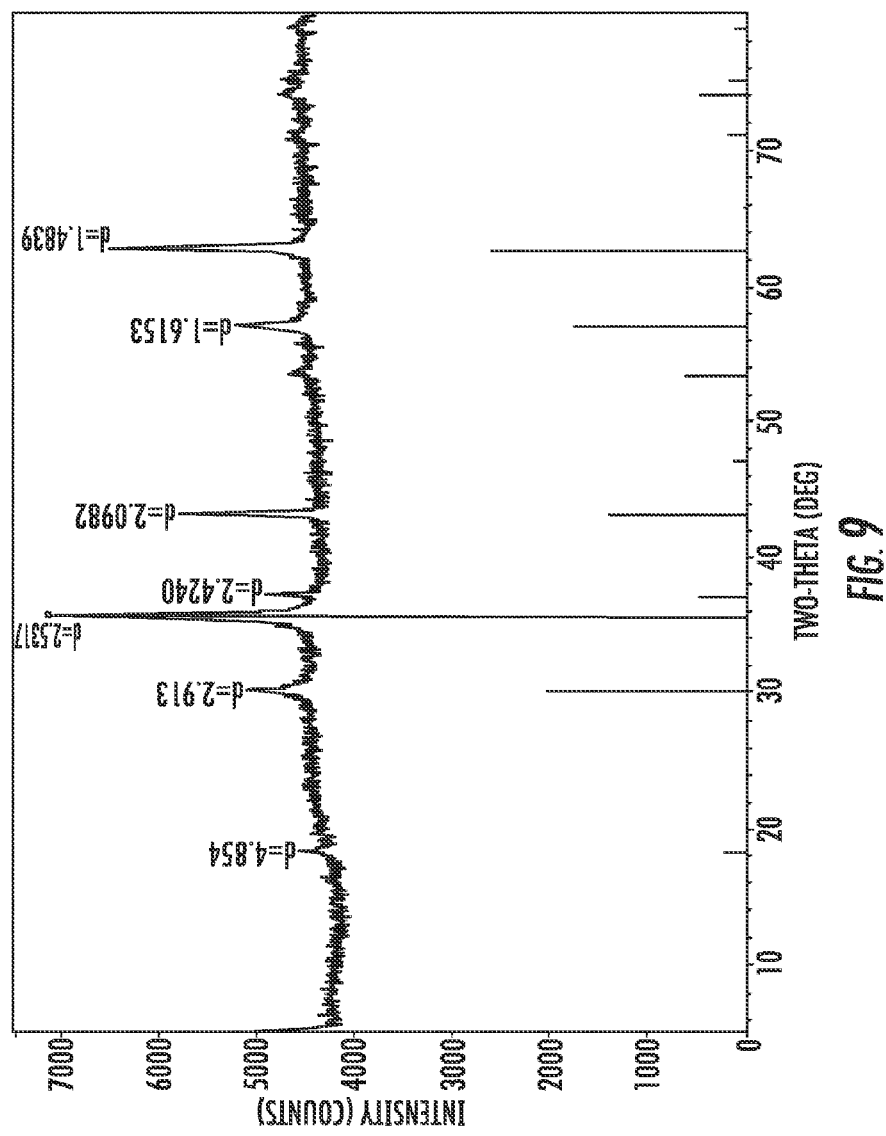
FIG. 9 shows an x-ray powder diffraction of the third disclosed composition, which shows well defined peaks corresponding to magnetite crystals.

The SEM/EDS analysis was also obtained for the third disclosed composition and appears very similar in its microstructure to the second disclosed composition. However, the discontinuous, spherical phase now has a diameter of about 500 nm as shown in FIG. 8, so this phase is larger than the equivalent phase in the second disclosed composition. Again, the x-ray powder diffraction plot in FIG. 9 shows well defined peaks corresponding to magnetite crystals.

In embodiments, the size of the magnetite crystals can be, for example, less than 1 micron. The disclosed glass ceramic composition or particles can be magnetized in the presence of an externally applied magnetic field. If liquid suspended particles are exposed to an externally applied magnetic field, the solid particles are attracted to the magnetic and liquid can be separated from the solid particles by removing the liquid. Following removal of the liquid, the particles presumably exhibit low remnant magnetization, since the separated particles readily re-suspend when contacted with a suitable liquid and in the absence of the external magnetic. This phenomenon can be advantageous in biomedical applications, such as disclosed herein, since the disclosed particles have a reduced tendency to agglomerate in the absence of the external magnetic field. The low cost to produce this glass ceramic makes it a superior material of choice compared to more expensive commercially available magnetic or magnetizable iron oxides.

In embodiments, the disclosed glass ceramic compositions can be magnetized in the presence of an externally applied magnetic field, and have low remnant magnetization in the absence of a magnetic field, which are both advantageous properties in certain biomedical applications.

In embodiments, the disclosed glass ceramic compositions can be batch melted in bulk and then ground to a desired particle size distribution resulting in a low cost alternative to the iron oxide particles presently used in biomedical applications.

In embodiments, the disclosed glass ceramic compositions are believed to have a unique chemical composition and microstructure.

EXAMPLES

The following Examples demonstrate making, use, and analysis of the disclosed glass ceramic compositions and methods in accordance with the above general procedures.

Example 1

Method of Making the First Composition ("1")

Composition 1 ("1") was batched with the following raw materials: 1,092 g of blast furnace slag (BFS) sand, 8 g of calcined alumina, 247 g of aluminum metaphosphate, 309 g of boric acid, 348 g of potassium carbonate, and 454 g of iron oxide. The batch was mixed for 15 mins in a Turbula® shaker mixer. The batch was loaded into a quartz crucible and melted at 1650° C. for 8 hr then poured onto a clean steel table to form a patty. The patty was then annealed for 8 hr at 600° C. and then allowed to cool to room temperature.

Method of Making Particles of the First Disclosed Composition

Figure 10:
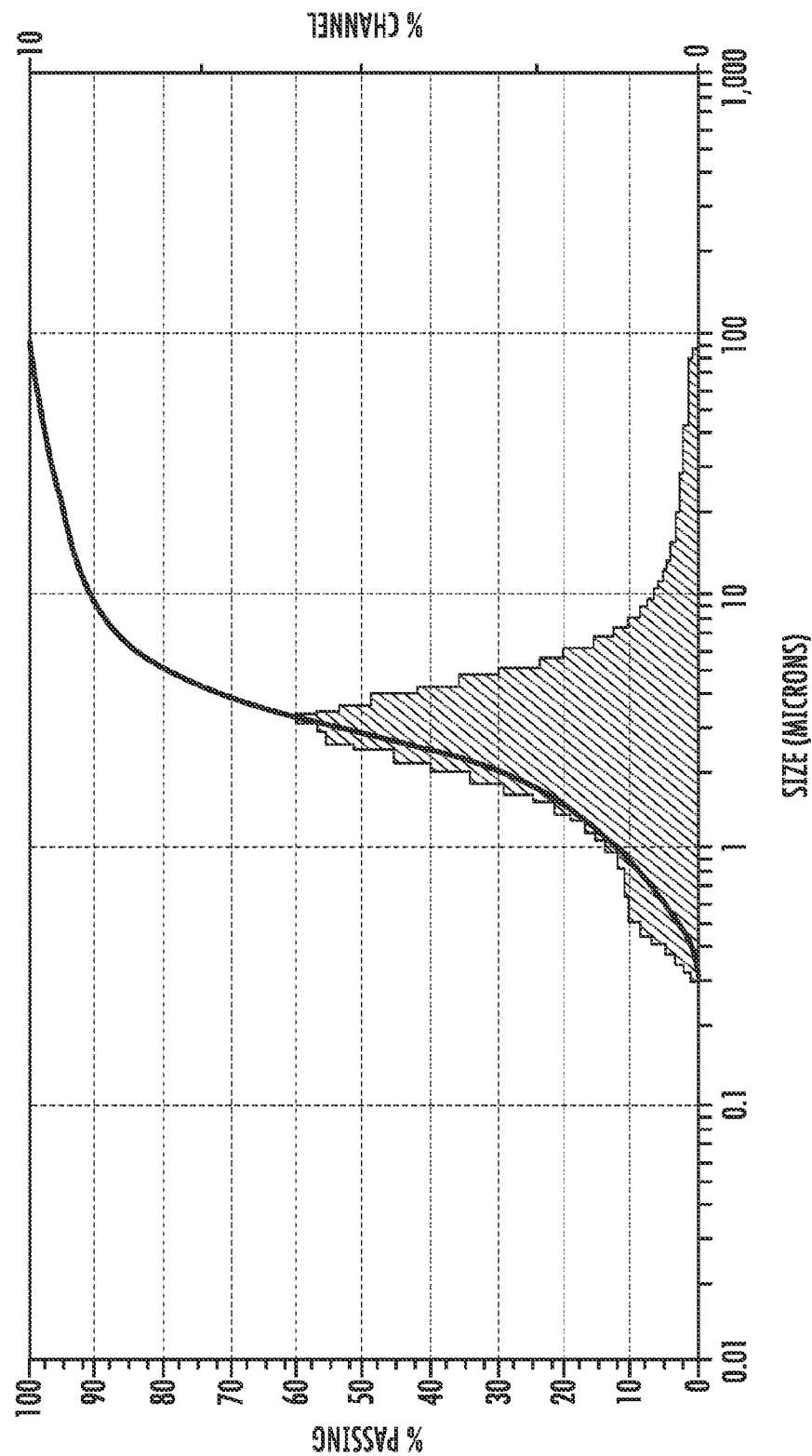
FIG. 10 shows an exemplary plot that shows a milled particle size distribution of a disclosed magnetizable composition having a D50 particle size (50% probability), i.e., an average size of 2.8 microns.

A jet mill feedstock was prepared as follows. 239 grams of the above annealed and cooled glass patty was coarsely broken up with a plastic hammer into small fragments (e.g., less than about ¼" inch largest size dimension) and put into an automatic mortar grinder until the product particles passed through a 20 mesh sieve. A jet mill was feed at a rate of about 24 g per hr and operated using compressed air to achieve a desired D50 target of from 1 to 3 microns. The jet milled product was then put through a 100 mesh sieve (150 microns) and the final particle size distribution was measured. FIG. 10 is an exemplary plot that shows a milled particle size distribution of a disclosed magnetizable composition having a D50 particle size (50% probability), i.e., an average size of 2.8 micron.

Example 2

Method of Making the Second Composition ("2")

Preparative Example 1 was repeated with the exception that composition 2 ("2") was batched with the following source materials: 373 g of BFS sand, 3 g of calcined alumina, 100 g of aluminum metaphosphate, 125 g of boric acid, 140 g of potassium carbonate, and 366 g of iron oxide. The batch was mixed for 15 mins in a Turbula® shaker mixer. The batch was loaded into a quartz crucible and melted at 1650° C. for 8 hr then poured onto a clean steel table to form a patty. The patty was then annealed for 8 hr at 700° C. and then allowed to cool to room temperature.

Method of Making Particles of the Second Composition

Particle preparative Example 1 was repeated with the exception that the above patty of composition 2 ("2") was used to prepare the jet mill feedstock.

Example 3

Method of Making the Third Composition ("3")

Preparative Example 1 was repeated with the exception that composition 3 ("3") was batched with the following source materials: 604 g of BFS sand, 6 g of calcined alumina, 197 g of aluminum metaphosphate, 247 g of boric acid, 278 g of potassium carbonate, and 1088 g of iron oxide. The batch was mixed for 15 mins in a Turbula® shaker mixer. The batch was loaded into a quartz crucible and melted at 1650° C. for 8 hr then poured onto a clean steel table to form a patty. The patty was then annealed for 8 hr at 600° C. and then allowed to cool to room temperature.

Method of Making Particles of the Third Composition ("3")

Particle preparative Example 1 was repeated with the exception that the above patty of composition 3 ("3") was used to prepare the jet mill feedstock.

Example 4

Prophetic

Use of the Second Composition ("2") in a Biomedical Application

The disclosed magnetizable glass ceramic compositions and their size-reduced particles can have a variety of uses and applications including, for example, nucleic acid purification (e.g., PCR, plasmid, genomic DNA, etc.), immunoprecipitation, exosome analysis, cell isolation, cell activation and expansion, nucleic acid isolation, rapid mRNA isolation, protein isolation, peptide purification, streptavidin-coupled magnetic beads, in vitro diagnostics assay development, drug delivery, and like applications, including non-life science related applications, such as magnetizable ink applications.

Example 5

Method of Magnetic Separation

Figure 11A:
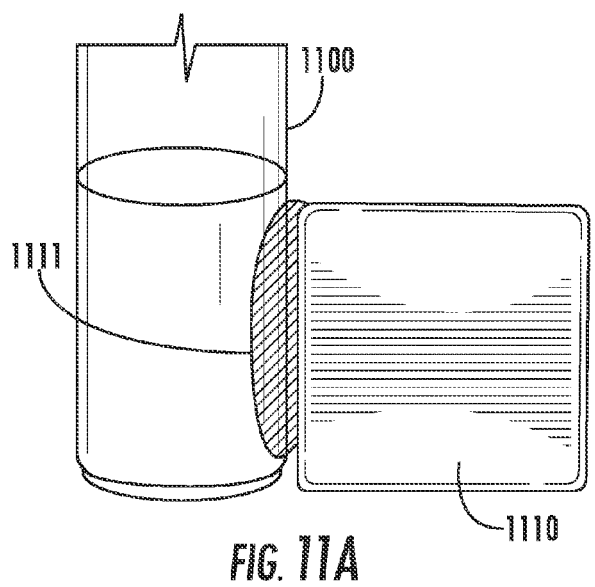
FIGS. 11A and 11B show images of a magnetic separation experiment demonstrating particle suspension, particle magnetization and aggregative collection (11A) in the presence of an external magnetic, and resuspension of the separated particles (11B).
Figure 11B:
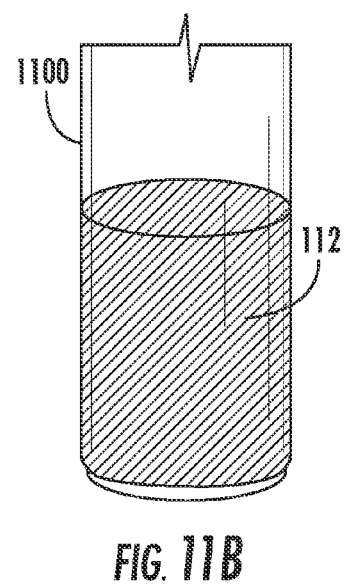

FIGS. 11A and 11B show images of a magnetic separation experiment. A standard magnetic separation experiment was accomplished, i.e., exposing a liquid suspension of the disclosed particles to an external magnet, decanting, and then re-suspending the particles in the absence of an external magnet. The particles readily re-suspended in the absence of an external magnet demonstrating a significant separation property of the magnetizable particles. Specifically, an opaque aqueous particle suspension prepared from ground particles of the third composition or sample "3" (see Example 3 above and Table 1) and water in a glass vial (1100) was exposed to an external bar magnet (1110) that resulted in particle magnetization and concentration of the particles (11A) (dark oblong bead and clarified liquid) (1111) in the wall area adjacent to the external magnet (adjacent monolith cube on right). The aqueous phase was removed from the aggregated particles, such as by decanting, pipetting, etc. The external magnet was removed. The aggregated particles readily resuspended when contacted with fresh aqueous phase (11B) (no dark oblong bead only a dark turbid or opaque suspension of particles) (1112). The particles behaved similarly after several cycles. The suspended particles when left undisturbed eventually settle to the bottom of the vial by gravity as seen with iron oxide particles having smaller diameters.

FIG. 12 show images of two different magnetizable glass ceramic compositions (top row is an aqueous suspension of composition "2"; and the bottom row is an aqueous suspension of composition "3") suspended in water in a magnetic separation experiment. The magnetic separation experiments demonstrate magnetizable glass ceramic composition particle suspensions (i.e., free suspension; 1200, 1210), and particle magnetization and aggregative collection (i.e., at t=0 (1220, 1230), 1 min (1240, 1250), and clean separation at 3 mins (1260, 1270)), in the presence of an external bar magnetic. In an exemplary magnetic separation experiment, 100 mg of jet-milled glass ceramic composition particles were suspended in 20 mL DI water in a capped glass vial and a first image of the free suspension was recorded with a camera. Next a bar magnet (1300) is placed in direct contact with the exterior wall of the vial containing the suspension, and a second (t=0) image was recorded with the camera. A third (t=1 min) image was recorded, and then a final fourth (t=3 min) image recorded with the camera. The time series of images show increasing collection of particles on the vial wall in the vicinity of the magnet, and increased clarity of the suspending liquid due to magnetic particle depletion from suspension and onto the wall in proximity of the magnetic.

The disclosure has been described with reference to various specific embodiments and techniques. However, it should be understood that many variations and modifications are possible while remaining within the scope of the disclosure.

What is claimed is:

1. A glass ceramic composition comprising:
    a continuous first glass phase comprising $SiO_2$, $B_2O_3$, $P_2O_5$, and $R_2O$;
    a discontinuous second glass phase comprising at least one of $SiO_2$, $B_2O_3$, $P_2O_5$, $R_2O$, or mixtures thereof; and
    a discrete magnetizable crystalline phase dispersed in the discontinuous second phase,
where $R_2O$ is selected from at least one of $K_2O$, $Li_2O$, $Na_2O$, or mixtures thereof.

2. The glass ceramic composition of claim 1 wherein the continuous first phase is enriched in $SiO_2$ relative to the discontinuous second glass phase, the discrete magnetizable phase, or both.

3. The glass ceramic composition of claim 1 wherein the continuous first glass phase is enriched in Si relative to the discontinuous second glass phase.

4. The glass ceramic composition of claim 1 wherein the discontinuous second glass phase is enriched in Fe and P relative to the continuous first glass phase.

5. The glass ceramic composition of claim 1 wherein the discrete magnetizable crystalline phase comprises discrete magnetite crystals comprising a plurality of at least one of $Fe^{2+}$ ions, $Fe^{3+}$ ions, $Fe^{2+}$ oxides, $Fe^{3+}$ oxides, or mixtures thereof.

6. The glass ceramic composition of claim 1 wherein $R_2O$ is $K_2O$.

7. A magnetizable glass ceramic composition, comprising:
    60 to 70% $SiO_2$,
    1 to 2% $Al_2O_3$,
    3 to 5% $P_2O_5$,
    5 to 8% $B_2O_3$,
    5 to 8% $R_2O$ where $R_2O$ is selected from at least one of $K_2O$, $Li_2O$, $Na_2O$, or mixtures thereof, and
    10 to 22% $Fe_2O_3$, based on a composition total of 100 mol %.

8. The magnetizable glass ceramic composition of claim 7 wherein the composition has a $Fe^{2+}$/total Fe mol ratio of 0.4 to 0.5.

9. The magnetizable glass ceramic composition of claim 7 wherein the composition includes a plurality of iron ions in mixed oxidation states.

10. The magnetizable glass ceramic composition of claim 9 wherein the plurality of iron ions in mixed oxidation states comprises magnetite crystals having a size of from 0.01 to 1 micrometer.

11. The magnetizable glass ceramic composition of claim 10 wherein the magnetite crystals are magnetized by an external magnetic field, and the resulting magnetized magnetite crystals lose magnetization in the absence of the external magnetic field.

12. The magnetizable glass ceramic composition of claim 7 wherein the composition has a melt temperature of from 1300 to 1600° C.

13. A method of making the magnetizable glass ceramic composition of claim 7, comprising:
    melting a mixture of a source of:
        60 to 70% $SiO_2$,
        1 to 2% $Al_2O_3$,
        3 to 5% $P_2O_5$,
        5 to 8% $B_2O_3$,
        5 to 8% $R_2O$ where $R_2O$ is selected from at least one of $K_2O$, $Li_2O$, $Na_2O$, and mixtures thereof,
        10 to 22% $Fe_2O_3$, based on a composition total of 100 mol %, and
    reducing the size of the resulting solidified melt into a particulate powder.

14. The method of making of claim 13, further comprising heat treating the melt mixture at from 500 to 800° C., for 1 to 24 hrs.

15. The method of making of claim 13, wherein the particulate powder has a particle size of from 1 to 100 microns.

16. The method of making of claim 13, wherein the particulate powder has a particle shape selected from at least one of: a sphere having a smooth surface; a sphere having a rough surface; an irregular or random shape; a shape having an aspect ratio of 1:1 to 1:5; or a mixture thereof.

17. The method of making of claim 13, wherein the melting is accomplished at from 1300 to 1700° C., for 1 to 10 hrs.

18. The method of making of claim 13, wherein the mixture has a mol ratio of $Fe^{2+}$ to total Fe of from 0.4 to 0.5.

19. An article comprising the glass ceramic composition of claim 1.

20. The article of claim 19 wherein the article is used in at least one of nucleic acid purification, immuno-precipitation, exosome analysis, cell isolation, cell activation and expansion, nucleic acid isolation, rapid mRNA isolation, protein isolation, peptide purification, streptavidin-coupled magnetic beads, in vitro diagnostics assay development, magnetizable ink, and combinations thereof.

* * * * *

UNITED STATES PATENT AND TRADEMARK OFFICE
CERTIFICATE OF CORRECTION

| | |
|---|---|
| PATENT NO. | : 10,059,621 B2 |
| APPLICATION NO. | : 15/603150 |
| DATED | : August 28, 2018 |
| INVENTOR(S) | : Timothy Michael Gross et al. |

It is certified that error appears in the above-identified patent and that said Letters Patent is hereby corrected as shown below:

On the Title Page

On page 2, Column 1, item (56), other publications, Line 25, delete "baed" and insert -- based --, therefor.

On page 2, Column 1, item (56), other publications, Line 26, delete "Sciemce:" and insert -- Science: --, therefor.

Signed and Sealed this
Twenty-sixth Day of April, 2022

*Katherine Kelly Vidal*

Katherine Kelly Vidal
*Director of the United States Patent and Trademark Office*